US00PP10241P

United States Patent [19]

Zaiger et al.

[11] Patent Number: Plant 10,241

[45] Date of Patent: Feb. 17, 1998

[54] NECTARINE TREE 'KAY GLO'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 772,579

[22] Filed: Dec. 24, 1996

[51] Int. Cl.[6] ..... A01H 5/00

[52] U.S. Cl. ..... Plt./41.1

[58] Field of Search ..... Plt./41.1

*Primary Examiner*—James R. Feyrer

[57] ABSTRACT

A new and distinct variety of nectarine tree (*Prunus persica* var. *nucipersica*) which has the following unique combination of desirable features:

1. Heavy and regular production of large size fruit.
2. Fruit with an attractive red skin color.
3. Early maturity of the fruit.
4. Fruit with good storage and shipping quality.
5. Vigorous, semi-upright growth.
6. Relatively uniform size fruit throughout the tree.
7. Fruit holding firm on the tree for approximately 7 to 10 days after maturity (shipping ripe).
8. Fruit with very good flavor and eating quality.

1 Drawing Sheet

ORIGIN OF THE VARIETY

The present new variety of nectarine tree was developed by us in our experimental orchard located near Modesto, Calif., as a second generation selection from the cross of a selected seedling with field identification number 46G24 with May Crest Peach (U.S. Plant Pat. No. 4064). The maternal parent (46G24) originated from an open pollinated May Grand Nectarine (U.S. Plant Pat. No. 2794) seedling. A large group of the second generation seedlings were planted, grown and maintained under close and careful observation by us. One seedling, which is the present variety, having especially desirable fruit characteristics, was selected for asexual reproduction and commercialization.

ASEXUAL REPRODUCTION OF THE VARIETY

Asexual reproduction of the new and distinct variety of nectarine tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

The present new variety of nectarine tree is of large size, vigorous, semi-upright growth and a productive and regular bearer of large, yellow flesh, clingstone fruit with attractive red skin color, and having very good flavor and eating quality. The fruit is further characterized by having very firm flesh, good handling and shipping quality, holding firm on the tree 7 to 10 days after shipping ripe, being relatively uniform in size at maturity and, in comparison to the May Grand Nectarine (U.S. Plant Pat. No. 2794), the new variety has greater production of larger size fruit, has less split pits and is approximately 3 to 4 days earlier in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of specimens grown near Modesto Calif., with color terminology. (except those in common terms) in accordance with Reinhold Color Atlas by A. Kornerup and J. H. Wanscher.

Tree:
- *Size.*—Large.
- *Vigor.*—Vigorous.
- *Form.*—Usually pruned to vase shape.
- *Productivity.*—Productive.
- *Bearer.*—Regular.
- *Density.*—Medium dense.
- *Growth.*—Semi-upright.

Trunk:
- *Size.*—Large.
- *Texture.*—Medium shaggy.
- *Color.*—Brown to grayish brown (5-E-5) to (5-F-5).

Branches:
- *Size.*—Medium.
- *Texture.*—Smooth to medium rough, varies with age of growth.
- *Lenticels.*—Numerous. Medium size.
- *Color.*—Light brown to brown (6-D-5) to (6-E-5).

Leaves:
- *Size.*—Large. Average length 6⅛". Average width 1½".
- *Form.*—Lanceolate.
- *Margin.*—Crenate.
- *Thickness.*—Medium.
- *Color.*—Upper surface — green to dark green (28-F-6) to (28-F-8). Lower surface — dull green to green (28-E-5) to (28-E-7).
- *Petiole.*—Medium length. Medium thickness.
- *Glands.*—Globose. Number varies from 0 to 3. Average number 2. Small size. Positioned on upper portion of petiole and base of leaf blade.
- *Surface.*—Smooth.

Flower buds:
- *Size.*—Large.
- *Length.*—Long.

*Form.*—Plump.

Flowers:

*Size.*—Large, showy.

*Pollen.*—Present, self-fertile.

*Blooming period.—Date of first bloom:* Mar. 6, 1996. *Date of full bloom:* Mar. 10, 1996. Varies slightly with climatic conditions.

*Color.*—Pink.

Fruit:

*Maturity when described.*—Firm ripe.

*Date of first picking.*—May 25, 1996.

*Date of last picking.*—May 30, 1996. Varies slightly with climatic conditions.

*Size.*—Large, comparatively uniform. Average diameter axially 3". Average transversely in suture plane 2⅞".

*Form.*—Globose, varies from globose to slightly elongated.

*Suture.*—Very shallow, extends from base to apex.

*Ventral surface.*—Nearly rounded.

*Apex.*—Rounded, varies from rounded to slightly retuse.

*Base.*—Retuse.

*Cavity.*—Rounded to slightly elongated in suture plane. Average depth 7/16". Average breadth 1"

Flesh:

*Ripens.*—Evenly.

*Texture.*—Very firm.

*Fibers.*—Few, small, tender.

*Aroma.*—Moderate.

*Amygdalin.*—Undetected.

*Eating quality.*—Very good, good balance between acid and sugar.

*Flavor.*—Very good.

*Color.*—Light yellow to butter yellow (4-A-4) to (4-A-5). Pit cavity, butter yellow to grayish yellow (4-A-5) to (4-B-5).

Skin:

*Thickness.*—Medium.

*Texture.*—Medium, tenacious to the flesh.

*Down.*—Wanting.

*Tendency to crack.*—None.

*Color.*—Ground — butter yellow to yellow orange (4-A-5) to (5-A-5). Overspread with madder red to red (9-A-7) to (9B-8).

Stone:

*Type.*—Clingstone.

*Size.*—Large. Average length 1½". Average width 1⅛". Average thickness ¾".

*Form.*—Ovoid to obovoid.

*Base.*—Usually rounded, varies from rounded to straight.

*Apex.*—Acuminate.

*Surface.*—Irregularly furrowed toward apex, pitted throughout, heavier toward the base, pits vary from round to elongated.

*Sides.*—Unequal.

*Tendency to split.*—Very slight.

*Color.*—Light brown to brown (5-C-6) to (5-D-6).

Use: Dessert. Market, local and long distance.

Keeping quality: Good.

Shipping quality: Good.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized to its large size, vigorous, semi-upright growth and a productive and regular bearer of large, firm, yellow flesh, clingstone fruit with very good flavor and eating quality; the fruit is further characterized by having very firm flesh with good handling and shipping quality, having an attractive red skin color and, in comparison to the May Grand Nectarine (U.S. Plant Pat. No. 2794), the new variety has greater production of larger size fruit, fewer split pits and is approximately 3 to 4 days earlier in maturity.

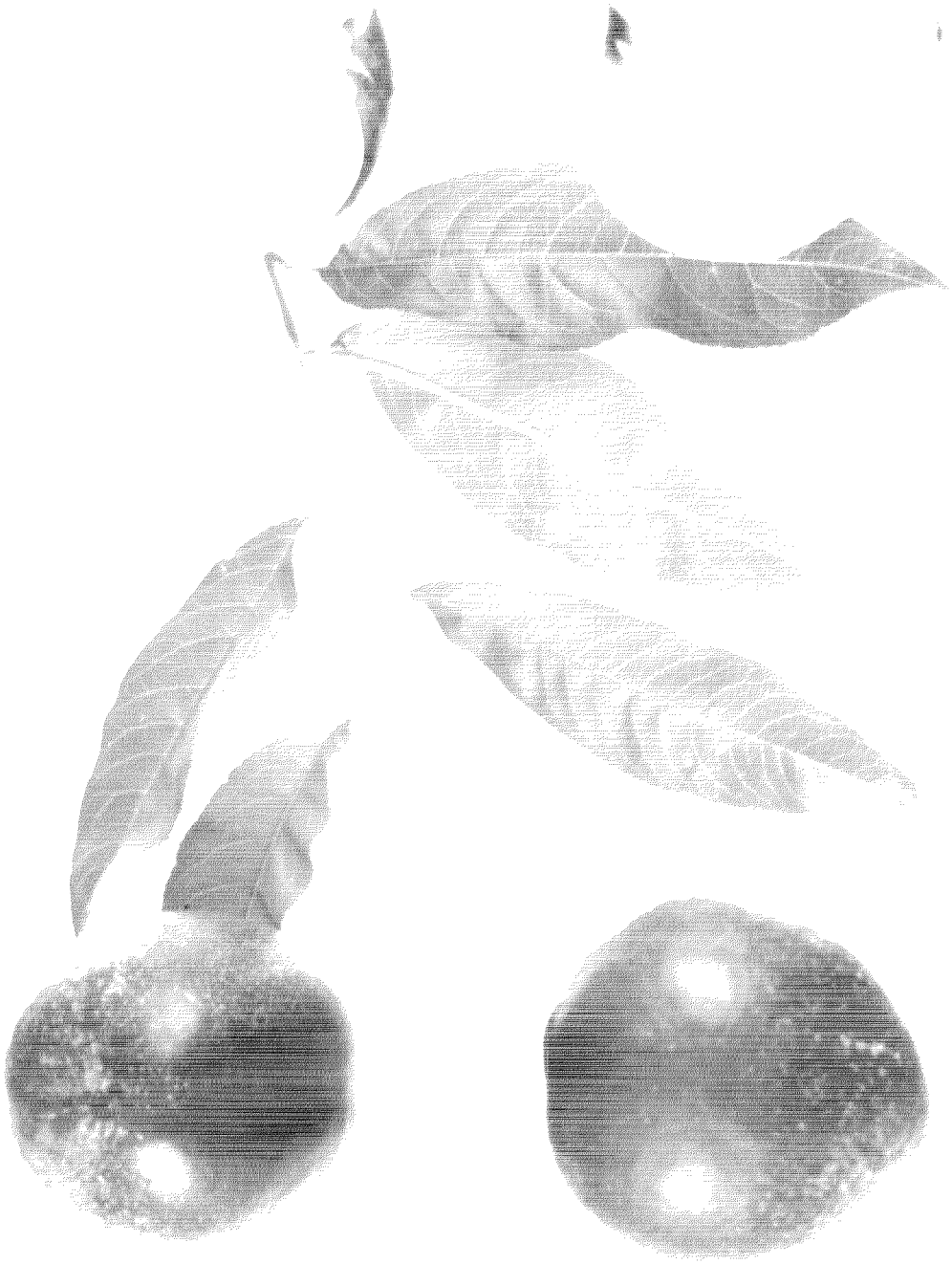

* * * * *